United States Patent [19]

Keane

[11] Patent Number: 4,886,355

[45] Date of Patent: Dec. 12, 1989

[54] COMBINED GLOSS AND COLOR MEASURING INSTRUMENT

[76] Inventor: Thomas J. Keane, 307 Twisted Stalk Dr., Gaithersburg, Md. 20878

[21] Appl. No.: 173,099

[22] Filed: Mar. 28, 1988

[51] Int. Cl.$^4$ .................. G01N 21/27; G01N 21/57
[52] U.S. Cl. ..................................... 356/73; 356/328; 356/445
[58] Field of Search ............... 356/73, 326, 328, 445, 356/446

[56] References Cited

U.S. PATENT DOCUMENTS

| | | | |
|---|---|---|---|
| 3,806,256 | 12/1974 | Ishak | 250/227 X |
| 3,890,049 | 6/1975 | Collins et al. | 356/445 X |
| 3,998,551 | 8/1976 | Suga | 356/73 |
| 4,040,743 | 6/1977 | Villaume et al. | 356/73 |
| 4,218,144 | 1/1980 | Whitehouse et al. | 356/446 |
| 4,222,064 | 9/1980 | Lodziński | 356/73 |
| 4,319,847 | 3/1982 | Howarth | 356/446 X |
| 4,464,054 | 8/1984 | Karras et al. | 356/446 X |
| 4,669,873 | 6/1987 | Wirz | 356/73 |
| 4,678,325 | 7/1987 | Lehtikoski et al. | 356/73 |

OTHER PUBLICATIONS

Budde, "A Reference Instrument for 20°, 60° and 85° Gloss Measurements", Metrologia 16, 1980, pp. 1–5.

*Primary Examiner*—Vincent P. McGraw
*Attorney, Agent, or Firm*—Lane & Aitken

[57] ABSTRACT

In an optical instrument for spectroscopically measuring color and gloss of a sample surface, a fiber optic probe is provided wherein light is transmitted from a light source to the probe through a fiber optic bundle. The fiber optic bundle is arranged to illuminate a surface positioned over an aperture in the probe. Light diffusely reflected from the sample surface is transmitted by a second fiber optic bundle to a spectrophotometer. A small fiber bundle is arranged in the probe to irradiate the surface of the sample at an angle of 60 degrees and a second small fiber bundle is arranged to receive light from the first mentioned small fiber bundle after being specularly reflected from the surface. The second fiber optic bundle transmits the received light to a photodetector in the spectrophotometer to provide an indication of the gloss of the sample surface.

15 Claims, 2 Drawing Sheets

COMBINED GLOSS AND COLOR MEASURING INSTRUMENT

BACKGROUND OF THE INVENTION

This invention relates to optical instruments and more particularly to an optical instrument designed to measure the color of a surface by measuring the diffuse reflectivity of the surface at different wavelengths throughout the visible spectrum and also to measure the gloss of the surface by measuring the specular reflectivity of the surface at a predetermined angle.

Color measurement of a surface is conventionally carried out by irradiating the surface and detecting the light diffusely reflected from the surface at different wavelengths throughout the visual spectrum. However, color perception is greatly affected by the gloss of the surface, that is the degree to which the surface reflects light specularly. Accordingly, there is a need for an optical instrument which will conveniently make color measurements on the diffusely reflected light from the surface as well as the specular reflectivity of the surface at the same place on that surface. The present invention provides an optical instrument which measures the color of a surface by spectroscopically measuring diffusely reflected light from the surface and which also measures the gloss of the surface by detecting light specularly reflected from the surface.

SUMMARY OF THE INVENTION

In accordance with the invention, a fiber optic probe is provided in which a plurality of fiber optic bundles are arranged to irradiate a test surface being measured and another fiber optic bundle is arranged to receive light diffusely reflected from the surface. In addition, a small fiber optic bundle is arranged to irradiate the surface with collimated light at an angle of 60 degrees and another small fiber optic bundle is arranged to receive light from the first mentioned small fiber optic bundle after being specularly reflected from the surface. The fiber optic bundle receiving the diffusely reflected light transmits the received light to a spectrometer, which detects the intensity of the diffusely reflected light at wavelengths incrementally spaced throughout the visual spectrum. The fiber optic bundle receiving the specularly reflected light transmits the received light to a photodetector which detects the intensity of the specularly reflected light. Signals representing the intensity values detected by the spectrometer are fed to a computer as is the signal generated by the photodetector representing the intensity of the specularly reflected light. The computer converts the intensity values represented by the signals applied thereto into measurements of the reflectivity of the surface at the different wavelengths incrementally spaced throughout the visual spectrum and into a measurement of the specular reflectivity or gloss of the surface.

The present invention thus provides an instrument which will conveniently measure the color and gloss of a common surface on a sample. The use of fiber optics in the instrument to transmit light to a sample surface transmit light reflected from the sample surface to photodetectors for both the color measurement and the gloss measurement facilitates the measurements on sample surfaces in a wide variety of applications. Also, the use of fiber optics to transmit light to and receive light from the sample surface in the gloss measurement facilitates the design of the source aperture for the light transmitted to the surface and the receptor aperture for light specularly reflected from the surface and enables a more even illumination of the source aperture to be achieved. In addition, use of fiber optics removes polarization from the light irradiating the sample surface for both measurements.

Further advantages of the invention will become readily apparent as the following detailed description of the invention unfolds and when taken in conjunction with the drawings.

DESCRIPTION OF A PREFERRED EMBODIMENT

Figure 1:
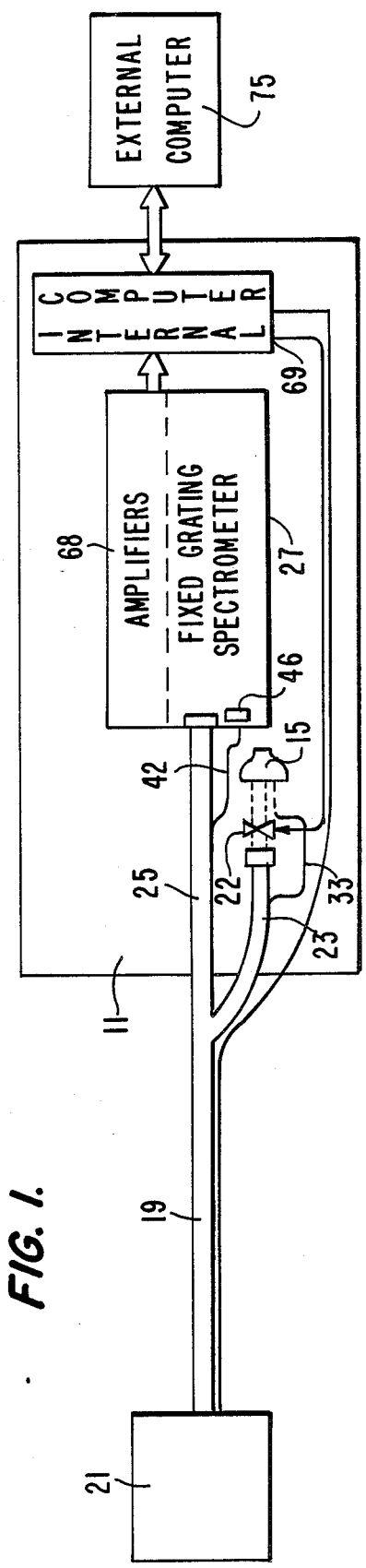
FIG. 1 is a schematic illustration of the instrument of the invention.

The instrument of the present invention is a modification of the instrument disclosed in copending application Ser. No. 868,700 filed May 30, 1986 entitled "Spectrometer with Combined Visible and Ultraviolet Sample Illumination" and invented by the inventor of this application. As shown in FIG. 1, the instrument comprises a câbinet 11 in which a source of visible light 15 is mounted to direct a beam of light through a shutter 22 onto the end of a fiber optic bundle 23, which carries the light through a flexible cable 19 to a probe 21. The source 15 also directs a portion of its beam onto the end of a small fiber optic bundle 33. The portion of the light directed onto the fiber optic bundle 33 does not pass through the shutter 22.

Figure 5:
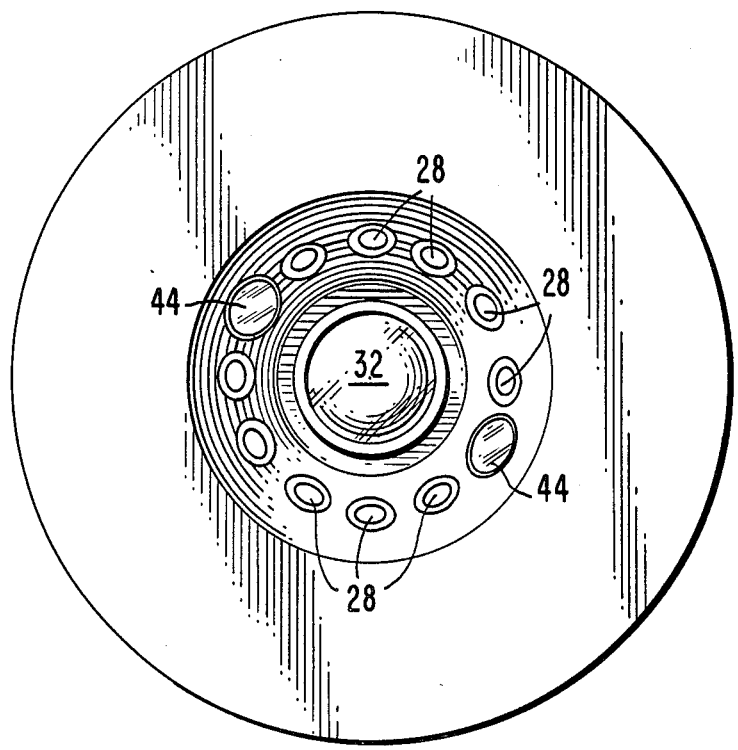
FIG. 5 is a view taken along the line 5—5 in FIG. 2 showing the top side of a fixture in the fiber optic probe.
Figure 6:
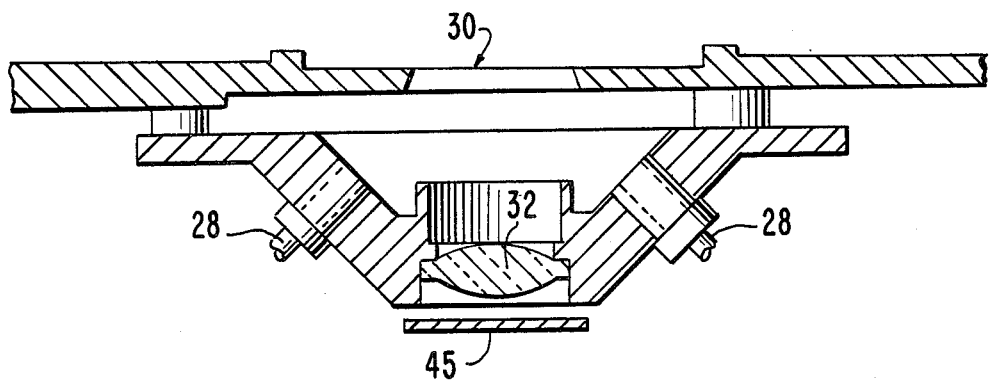
FIG. 6 is a sectional view in elevation taken along the line 6—6 in FIG. 2.

In the probe 21, the fiber optic bundle 23 is separated into 10 round bundles 28, the ends of which are mounted in a fixture 29, as shown in FIG. 5 and 6. The ends of the bundles 28 are distributed at 30 degree angles around an opening 30 in the probe, except that at two diametrically opposite positions, a 60 degree space is left between the adjacent pairs of bundle ends to leave room for the gloss measurement optics. The ends of the bundles 28 are arranged to direct light at an angle of 45 degrees onto the plane of the opening 30. In the preferred embodiment, a lens 32 may be mounted in the fixture 29 on the axis thereof to focus light diffusely reflected vertically from the surface of a sample placed over the opening 30 onto the end of a fiber optic bundle 25. When the sample surface to be measured has a large area, the lens 32 is not needed and may be omitted from instruments designed for such large area measurements. Alternatively, the lens 32 may be made selectively removable. The fiber optic bundle 25 carries the received light back through the cable 19 to the cabinet 11 and into the entrance slit of a spectrometer 27 within the cabinet 11. The end of the fiber optic bundle 25 which transmits the light into the spectrometer 27 is shaped into the entrance slit for the spectrometer 27 and is positioned to irradiate a fixed optical grating within the spectrometer 27. The details of the spectrometer 27 are disclosed in the above mentioned copending application.

Figure 2:
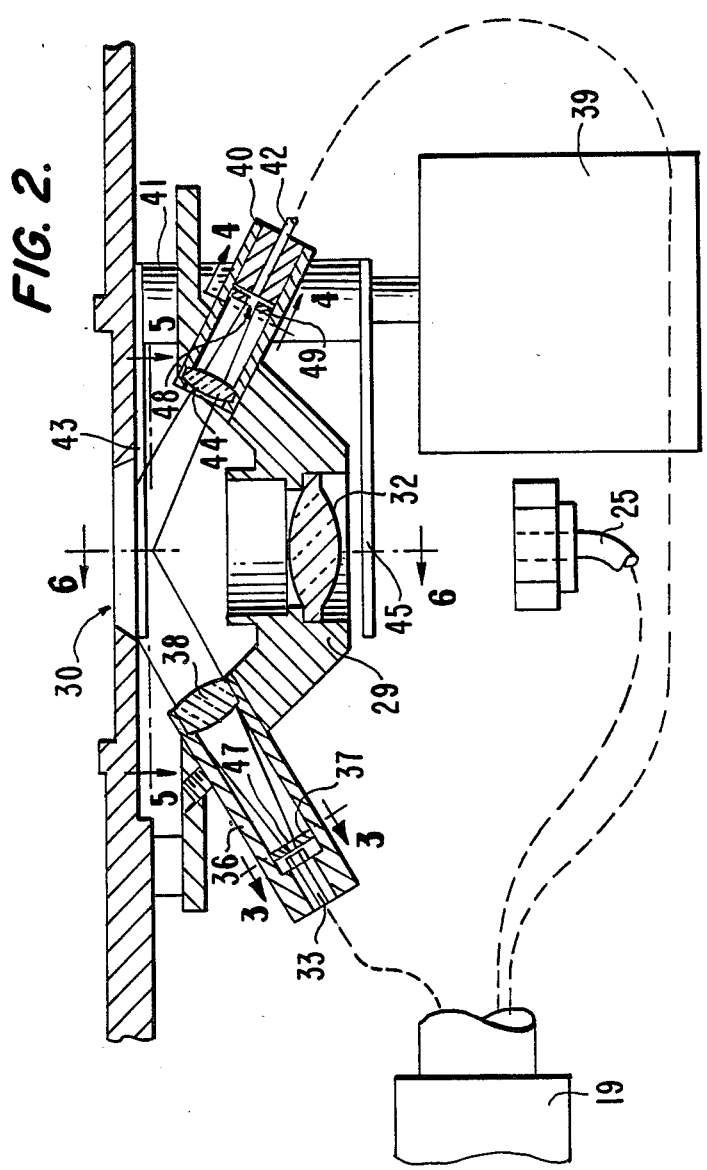
FIG. 2 is a partial sectional view in elevation of the fiber optic probe employed in the system of FIG. 1.

The small optic fiber bundle 33 carries light from the source 15 through the cable 19 to its transmitting end, which is mounted in the probe 21 in a mounting tube 36 with the bundle 33 positioned on the axis of the mounting tube 36 as shown in FIG. 2. The mounting tube 36 is mounted in the fixture 29 in the center of one of the two 60 degree spaces between adjacent bundles 28 and is oriented so that the transmitting end of the fiber optic bundle 33 is pointed at the center of the opening 30 at an angle of 60 degrees to normal to the plane of the opening 30. A mask 37 defining a source aperture 47 is mounted in the tube 36 spaced a small distance from the transmitting end of the fiber optic bundle 33. Because the end of the fiber optic bundle is made of individual fibers, the beam of light emitted from the fiber optic bundle 33 is actually a multiplicity of separate tiny beams of light. The space between the end of the fiber optic bundle 33 and the mask 37 allows the tiny beams to mix together so that the aperture 47 is substantially uniformly illuminated and a uniform beam of light is projected from the aperture 47 toward the opening 30. The use of fiber optics to illuminate the source aperture 47 achieves a high degree of uniformity of illumination of the source aperture 47 compared to source apertures illuminated by incandescent filaments. Incandescent filaments tend to have variations in the light intensity emitted over the length of the filament, so that when one is used to illuminate a source aperture, some degree of non-uniformity in the intensity of the illumination over the area of the aperture occurs. More uniform illumination is achieved with the present invention because each optic fiber in the bundle 33 will emit a beam of substantially the same intensity as the other optic fibers in the bundle. Accordingly, when these beams of uniform intensity mix together at the source aperture 47, uniform illumination is achieved.

At the inner end of the mounting tube 36, there is mounted a lens 38 to collimate light transmitted through the aperture 47 and direct the light in a beam of parallel rays toward the center of the opening 30. Opposite the mounting tube 36 in the fixture 29 in the other 60 degree space between adjacent bundles 28 is a mounting tube 40, in which the end of a small fiber optic bundle 42 is mounted at the outer end of the tube 40 on the axis thereof. The end of the fiber optic bundle 42 is also pointed at the center of the opening 30 at an angle of 60 degrees to normal to the plane of the opening 30. A mask 49 defining a receptor aperture 48 is mounted in the tube 40 spaced a short distance from the end of the optic fiber bundle 42. The inner end of the mounting tube 40 contains a lens 44, which will focus light received from the center of the surface of a sample placed over the opening 30 on the aperture 48. The axes of the mounting tubes 36 and 40 are in a common plane, perpendicular to the plane of the opening 30, so that light from the source aperture 47 in the mask 37 irradiating the center of a sample placed over the opening 30 and specularly reflected therefrom will be focused within the receptor aperture 48 in the mask 49.

Figure 3:
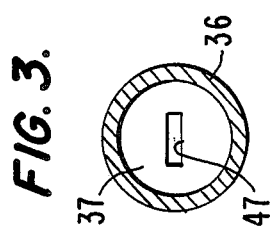
FIG. 3 is an enlarged sectional view taken along line 3—3 in FIG. 2 to show the shape of a transmitting aperture for the gloss measurement.
Figure 4:
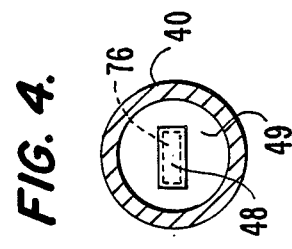
FIG. 4 is an enlarged cross sectional view taken along the line 4—4 in FIG. 2 to show the shape of a receptor aperture for the gloss measurement.

As shown in the enlarged sectional view of FIG. 3, the source aperture 47 in the mask 37 is rectangular in shape. Light from the fiber optic bundle 33 after passing through the source aperture 47 is caused to illuminate the sample and for a polished sample placed over the opening 30, a rectangular image of source aperture 47 is formed at the receptor aperture 48. As shown in FIG. 4, the receptor aperture 48 also has a rectangular shape corresponding to the rectangular shape of the source aperture 47. Also as shown in FIG. 4, the lens 44 focuses an image 76 in the middle of the receptor aperture 48 of the specular reflection from the spot of light illuminated on a surface of a sample placed over the opening 30 by light from the fiber optic bundle 33. The receptor aperture 48 must be at least as large as the image and preferably is slightly larger than the image as shown in FIG. 4. The exact sizes and ratios of the source and receptor apertures will generally correspond to those cited by such standardizing bodies as, ASTM, BSO, JIC, ISO et al.

When gloss is being measured, the shutter 22, which is controlled by a computer 69, is closed so that the only light irradiating the sample is transmitted through the small fiber optic bundle 33 and the source aperture 47. Thus, substantially all of the light received by the receptor aperture 48 will be specularly reflected light from the illumination of the sample surface by the fiber optic bundle 33. The light passing through the receptor aperture 48 is received by the fiber optic bundle 42, which carries the specularly reflected light back through the cable 19 to the cabinet 11 and into the housing of the spectrometer 27, where it is arranged to irradiate a photocell 46. Thus, the photocell 46 will detect the intensity of the light specularly reflected from a sample positioned over the aperture 30. Because of the uniform illumination of the source aperture achieved by the use of fiber optics, the illumination of the sample over the illuminated area is very uniform. As a result the gloss measurement is less subject to variation caused by surface irregularities.

As described in the above-mentioned copending application, signals from the photodetectors of the fixed array in the spectrometer 27 are amplified by amplifiers 68 located in the housing of the spectrometer 27 and applied to the computer 69, which is referred to as the internal computer. One of the amplifiers 68 will amplify the output signal of the photodetector 46 and apply this amplified signal to the internal computer 69. The internal computer 69 is connected to an external computer 75, which provides a display of the measurements and applies signals to the internal computer 69 in response to keyboard actuation to control the operation of the instrument.

As in the above-mentioned copending application, the probe 21 has mounted therein, a stepper motor 39, which has mounted on its output shaft 41, two paddles 43 and 45. Paddle 43 has mounted in one end thereof a circular white standard sample approximately the same size as the opening 30 and the paddle 43 is pivotable by the stepper motor 39 via the shaft 41 to a position in which the white standard sample is aligned with the opening 30 just inside the opening 30 within the housing of the probe 21. When the paddle 43 is pivoted to position the white standard sample aligned with the opening 30, the light emitted from the bundle ends 28 will irradiate the white standard sample and be diffusely reflected therefrom to be received by the fiber optic bundle 25. The resulting amplified signals produced by the array of photodetectors in the spectrometer 27 are processed by the internal computer 69 to determine calibration factors. As explained in the above-mentioned copending application, these calibration factors are used to correct the amplified output signals from the photodetector array when an unknown sample is being measured and compensate for temperature changes.

If the stepper motor 39 pivots the paddle 43 past the opening 30, it will bring the paddle 45 into position to block any light transmission between the lens 32 and the receiving end of the fiber optic bundle 25. The paddle 45 is opaque and is used to obtain null values for the spectrometer 27, in the manner explained in the copending application.

With the instrument described above, a measurement of the color of a sample surface and a measurement of the gloss of the surface are made sequentially at very nearly the same time. When the color measurement is being made, the computer 69 opens the shutter 22, and immediately thereafter or therebefore, the computer 69 closes the shutter 22 to make a gloss measurement. Depending on the reflectivity of the sample, when a color measurement is being made, some light will be diffusely reflected to the receiving end of the fiber optic bundle 25 as a result of the irradiation of the sample through the optic fiber 33, but this light will be taken into account in the normal calibration of the instrument for diffuse reflectance.

During the gloss measurement the only light transmitted to the sample surface will be through the fiber optic bundle 33. Some of this light will be diffusely reflected from the surface of the sample to the receiving end of the fiber optic bundle 42 in addition to the specularly reflected light. However, the amount of this light generally will be small relative to the intensity of the specularly reflected light and the diffusely reflected light, can be mathematically subtracted in the instrument measurements by the following relationship:

$$R_s' = R_s - kR_D$$

in which:

$R_s'$ = corrected specular reflectance measurement
$R_s$ = specular reflectance measured by the instrument
$R_D$ = Luminous diffuse reflectance ($V\lambda$) for the sample as measured by the instrument
$k$ = a fraction determined by the ratio of the diffuse energy received by the receptor aperture to that of the total diffuse hemispherical reflectance of a perfect lambertian reflector.

The above description is of a preferred embodiment of the invention and many modifications may be made thereto without departing from the spirit and scope of the invention which is defined in the appended claims.

What is claimed is:

1. An instrument for measuring gloss and color of a sample surface comprising a probe defining a position to receive a sample surface to be measured, a source of visible light, a first fiber optic bundle arranged to receive light from said source and irradiate a sample surface received at said position with light from said source, said bundle including a plurality of fibers having transmitting ends pointed at said sample surface so as to illuminate said sample surface at a first angle, a second fiber optic bundle having a transmitting end pointed at said sample surface so as to irradiate said sample surface with light transmitted through said second fiber optic bundle at a second angle different than said first angle, first fiber optic means positioned to receive light diffusely reflected from said surface as a result of irradiation of said surface by said first fiber optic bundle, second fiber optic means arranged to receive light from said second fiber optic bundle and specularly reflected from said surface, means to detect the intensity of light received by said first fiber optic means, and means to detect the intensity of light received by said second fiber optic means.

2. An optical instrument as received in claim 1, wherein said second fiber optic bundle irradiates said sample surface with light received from said source of visible light.

3. An optical instrument as received in claim 1, wherein said means to detect the intensity of light received by said first optic means comprises means to detect the intensity of the light at different wavelengths distributed throughout a visible spectrum.

4. An optical instrument as recited in claim 1, wherein said first fiber bundle and said second fiber optic bundle are arranged so that said second fiber optic means receives specularly reflected light from only said second fiber optic bundle.

5. An optical instrument as recited in claim 4, wherein said second fiber optic means comprises a third fiber optic bundle.

6. An optical instrument as recited in claim 5, wherein said first fiber optic means comprises a fourth fiber optic bundle.

7. An optical instrument as recited in claim 1, wherein said means to detect the intensity of light received by said second fiber optic means comprises a photodetector, said second fiber optic means comprises a third fiber optic bundle arranged to transmit the light received by said second fiber optic means to said photodetector, said means to detect the intensity of light received by said first fiber optic means comprises a spectrometer at the location of said photodetector, and said first fiber optic means comprises a fourth fiber optic bundle arranged to transmit the received light to an entrance slit of said spectrometer.

8. An optical instrument as recited in claim 7, wherein said photodetector is located within the housing of said spectrometer.

9. An optical instrument as recited in claim 1, wherein a lens is mounted in said probe to focus the light from said second fiber optic bundle and specularly reflected from said sample surface to be received by said second fiber optic means.

10. An optical instrument as recited in claim 1, wherein there is provided a lens mounted in said probe arranged to collimate the light emitted from said second fiber optic bundle and irradiate said sample surface with collimated light at said second angle.

11. An optical instrument as recited in claim 1, wherein there is provided a mask defining a source aperture spaced from said transmitting end of said second fiber optic bundle and arranged to be illuminated by light transmitted in straight lines without any change in direction from said transmitting end to said source aperture, and means defining a receptor aperture having a predetermined size and a shape which corresponds to the shape of said source aperture, said receptor aperture being positioned in the path of light specularly reflected from said spot to said second fiber optic means.

12. An optical instrument as recited in claim 11, wherein a second lens is mounted in said probe arranged to focus light emitted from said second fiber optic bundle and specularly reflected from said sample surface onto said receptor aperture.

13. An optical instrument for measuring gloss of a surface comprising a probe defining a position to receive a sample surface to be measured, a source of visible light, a fiber optic bundle arranged to receive light from said source and illuminate said surface at a predetermined angle, said fiber optic bundle having a transmitting end pointed toward a sample surface received in said position, a mask defining a source aperture spaced from said transmitting end and arranged to be illuminated by light transmitted in straight lines without any change in direction from said transmitting end to said source aperture, light receiving means positioned to receive light from said fiber optic bundle and specularly reflected from said sample surface.

14. An optical instrument as recited in claim 13 further comprising means defining a receptor aperture having a predetermined size and a shape which corresponds to the shape of said source aperture, said receptor aperture being positioned in the path of light from said source aperture and specularly reflected from said surface to said light receiving means.

15. An optical measuring instrument as recited in claim 1, wherein there is provided a mask defining a source aperture spaced from said transmitting end of said fiber optic bundle and arranged to be illuminated by light transmitted in straight lines without any change in direction from said transmitting end to said source aperture, said second fiber optic means receiving light passing through said source aperture and specularly reflected from said surface.

* * * * *